United States Patent
Razavi et al.

(10) Patent No.: US 9,700,233 B2
(45) Date of Patent: Jul. 11, 2017

(54) METHOD AND SYSTEM TO EQUALIZING CARDIAC CYCLE LENGTH BETWEEN MAP POINTS

(71) Applicant: Pacesetter, Inc., Sunnyvale, CA (US)

(72) Inventors: Hoda Razavi, San Jose, CA (US); Yelena Nabutovsky, Mountain View, CA (US)

(73) Assignee: Pacesetter, Inc., Sunnyvale, CA (US)

(*) Notice: Subject to any disclaimer, the term of this patent is extended or adjusted under 35 U.S.C. 154(b) by 161 days.

(21) Appl. No.: 14/703,744

(22) Filed: May 4, 2015

(65) Prior Publication Data

US 2015/0313550 A1 Nov. 5, 2015

Related U.S. Application Data

(60) Provisional application No. 61/988,763, filed on May 5, 2014.

(51) Int. Cl.
A61B 5/04 (2006.01)
A61B 5/06 (2006.01)
A61B 5/00 (2006.01)
A61B 5/11 (2006.01)
A61B 5/042 (2006.01)

(52) U.S. Cl.
CPC ............ *A61B 5/062* (2013.01); *A61B 5/0422* (2013.01); *A61B 5/1107* (2013.01); *A61B 5/7232* (2013.01); *A61B 5/7278* (2013.01); *A61B 5/742* (2013.01); *A61B 5/04012* (2013.01); *A61B 5/7289* (2013.01)

(58) Field of Classification Search
CPC . A61B 5/1107; A61B 5/0044; A61B 5/04012; A61B 5/0452; A61B 5/721; A61B 5/7232; A61B 5/742; A61B 6/4441
See application file for complete search history.

(56) References Cited

U.S. PATENT DOCUMENTS

| | | |
|---|---|---|
| 5,391,199 A | 2/1995 | Ben-Haim |
| 5,713,367 A | 2/1998 | Arnold et al. |
| 6,233,476 B1 | 5/2001 | Strommer et al. |
| 6,301,496 B1 | 10/2001 | Reisfeld |

(Continued)

FOREIGN PATENT DOCUMENTS

| | | |
|---|---|---|
| EP | 1 070 480 A2 | 1/2001 |
| EP | 1 508 300 A1 | 2/2005 |

(Continued)

OTHER PUBLICATIONS

USPTO, "Notice of Allowance for U.S. Appl. No. 14/270,176", mailed May 20, 2016.

(Continued)

*Primary Examiner* — Amanda Patton
(74) *Attorney, Agent, or Firm* — Theresa A. Raymer

(57) ABSTRACT

A method and system are provided for equalizing cycle lengths among different map points during mapping studies. Different embodiments may be applicable to different circumstances and physiological settings. A compression embodiment encapsulates the entire behavior of a map point throughout its native cycle length. A truncation and rotation embodiment, and an extension and rotation embodiment allow for a more physiologically-relevant processing of the motion data.

20 Claims, 5 Drawing Sheets

(56) References Cited

U.S. PATENT DOCUMENTS

| | | |
|---|---|---|
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,397 B2 | 8/2007 | Hauck et al. |
| 7,276,064 B2 | 10/2007 | Paul et al. |
| 7,338,486 B2 | 3/2008 | Sliwa et al. |
| 7,386,339 B2 | 6/2008 | Strommer et al. |
| 7,505,809 B2 | 3/2009 | Strommer et al. |
| 7,697,973 B2 | 4/2010 | Strommer et al. |
| 7,881,769 B2 | 2/2011 | Sobe |
| 8,016,764 B1 | 9/2011 | Shelchuk |
| 8,195,292 B2 | 6/2012 | Rosenberg et al. |
| 8,849,381 B2 | 9/2014 | Mason et al. |
| 9,162,067 B1 | 10/2015 | Farazi et al. |
| 2003/0093067 A1 | 5/2003 | Panescu |
| 2003/0233039 A1 | 12/2003 | Shao et al. |
| 2005/0154282 A1 | 7/2005 | Li et al. |
| 2006/0245536 A1 | 11/2006 | Boing |
| 2007/0055142 A1* | 3/2007 | Webler .................. A61B 5/06 600/425 |
| 2007/0073179 A1 | 3/2007 | Afonso et al. |
| 2007/0100332 A1 | 5/2007 | Paul et al. |
| 2007/0106146 A1 | 5/2007 | Altmann et al. |
| 2007/0181139 A1 | 8/2007 | Hauck |
| 2007/0244479 A1 | 10/2007 | Beatty et al. |
| 2007/0270705 A1 | 11/2007 | Starks |
| 2007/0299352 A1 | 12/2007 | Harlev |
| 2008/0009758 A1 | 1/2008 | Voth |
| 2008/0091193 A1 | 4/2008 | Kauphusman et al. |
| 2008/0190438 A1 | 8/2008 | Harlev |
| 2009/0163904 A1 | 6/2009 | Miller et al. |
| 2009/0171345 A1 | 7/2009 | Miller et al. |
| 2009/0275828 A1 | 11/2009 | Shachar et al. |
| 2010/0168550 A1 | 7/2010 | Byrd et al. |
| 2010/0268059 A1 | 10/2010 | Ryu |
| 2011/0190593 A1 | 8/2011 | McNair et al. |
| 2011/0208038 A1 | 8/2011 | Konofagou et al. |
| 2011/0243401 A1 | 10/2011 | Zabair et al. |
| 2012/0184863 A1 | 7/2012 | Harlev et al. |
| 2013/0222415 A1 | 8/2013 | Vilsmeier et al. |
| 2013/0272592 A1 | 10/2013 | Eichler et al. |
| 2015/0045867 A1 | 2/2015 | Krishnan et al. |
| 2015/0133802 A1 | 5/2015 | Nabutovsky et al. |
| 2015/0141765 A1 | 5/2015 | Razavi et al. |
| 2015/0141858 A1 | 5/2015 | Razavi et al. |

FOREIGN PATENT DOCUMENTS

| | | |
|---|---|---|
| EP | 2 757 528 A1 | 7/2014 |
| WO | 97/24981 | 7/1997 |
| WO | 2012/090148 A1 | 7/2012 |

OTHER PUBLICATIONS

Notice of Allowance mailed Jun. 22, 2015; Related U.S. Appl. No. 14/328,523.
Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/U52015/028206 (Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731, filed Jun. 30, 1998 for "Chamber Mapping System".
Advisory Action mailed Aug. 10, 2015; Related U.S. Appl. No. 12/347,216.
Amendment filed Jun. 25, 2015; Related U.S. Appl. No. 12/347,216.
Final Office Action mailed May 4, 2015; Related U.S. Appl. No. 12/347,216.
Amendment filed Dec. 18, 2014; Related U.S. Appl. No. 12/347,216.
Non-Final Office Action mailed Oct. 2, 2014; Related U.S. Appl. No. 12/347,216.
Advisory Action mailed May 1, 2014; Related U.S. Appl. No. 12/347,216.
Amendment filed Apr. 24, 2014; Related U.S. Appl. No. 12/347,216.
Applicant Interview Summary, Apr. 21, 2014; Related U.S. Appl. No. 12/347,216.
Final Office Action mailed Feb. 25, 2014; Related U.S. Appl. No. 12/347,216.
Amendment filed Feb. 4, 2014; Related U.S. Appl. No. 12/347,216.
Non-Final Office Action mailed Nov. 21, 2013; Related U.S. Appl. No. 12/347,216.
Amendment filed Oct. 29, 2012; Related U.S. Appl. No. 12/347,216.
Advisory Action mailed Oct. 11, 2012; Related U.S. Appl. No. 12/347,216.
Amendment filed Oct. 1, 2012; Related U.S. Appl. No. 12/347,216.
Advisory Action mailed Sep. 12, 2012; Related U.S. Appl. No. 12/347,216.
Amendment filed Aug. 28, 2012; Related U.S. Appl. No. 12/347,216.
Final Office Action mailed Jun. 29, 2012; Related U.S. Appl. No. 12/347,216.
Amendment filed May 14, 2012; Related U.S. Appl. No. 12/347,216.
Interview Summary, Feb. 28, 2012; Related U.S. Appl. No. 12/347,216.
Non-Final Office Action mailed Feb. 13, 2012; Related U.S. Appl. No. 12/347,216.
Notice of Allwance mailed Feb. 25, 2016; Related U.S. Appl. No. 14/328,513.
Notice of Allowance mailed Feb. 25, 2016; Related U.S. Appl. No. 14/703,760.
Non-Final Office Action mailed Mar. 26, 2016; Related U.S. Appl. No. 14/703,749.
Notice of Allowance mailed Apr. 19, 2016; Related U.S. Appl. No. 14/270,161.
Non-Final Office Action mailed Dec. 11, 2015; Related U.S. Appl. No. 14/703,460.
Non-Final Office Action mailed Sep. 30, 2015; Related U.S. Appl. No. 14/270,181.
Notice of Allowance mailed Dec. 8, 2015; Related U.S. Appl. No. 12/347,216.
Final Office Action mailed Jan. 22, 2016; Related U.S. Appl. No. 14/270,176.
Non-Final Office Action mailed Feb. 8, 2016; Related U.S. Appl. No. 14/270,181.
Notice of Allowance mailed Oct. 27, 2015; Related U.S. Appl. No. 14/328,523.
University of California, SF, "History of AF Ablation", https://cardiology.ucsf.edu/care/clinical/electro/ablation_hist.html, accessed on Jan. 17, 2017.
USPTO, "Final Office Action for U.S. Appl. No. 14/703,749", Date mailed Jan. 23, 2017.
USPTO, "Non-Final Office Action for U.S. Appl. No. 14/270,186", Date mailed Feb. 27, 2017.
USPTO, "Non-Final Office Action for U.S. Appl. No. 14/478,707", Date mailed Mar. 2, 2017.
USPTO, "Non-Final Office Action for U.S. Appl. No. 14/703,735", Date mailed Jan. 12, 2017.
USPTO, "Non-Finnal Office Action U.S. Appl. No. 14/703,757", Date mailed Apr. 6, 2017.

* cited by examiner

METHOD AND SYSTEM TO EQUALIZING CARDIAC CYCLE LENGTH BETWEEN MAP POINTS

RELATED APPLICATION DATA

The present application relates to and claims priority from the following application: U.S. provisional application Ser. No. 61/988,763, filed May 5, 2014, titled "METHOD AND SYSTEM TO EQUALIZING CARDIAC CYCLE LENGTH BETWEEN MAP POINTS", which is expressly incorporated herein by reference in its entirety in the present application.

BACKGROUND OF THE INVENTION

Embodiments of the present disclosure generally relate to analyzing electrical and mechanical cardiac data, and more particularly to equalizing cardiac cycle length between different map points.

Current cardiovascular navigation systems, such as the St. Jude Medical MediGuide™ (MDG) cardiovascular navigation system, use fluoroscopic imaging in connection with three dimensional electromagnetic navigation to provide real-time position and orientation of a tool while in a region of interest. The MDG system is integrated with the fluoroscopic imaging system and tracks the sensors continuously within the imaging volume of the fluoroscopic system, on both live fluoroscopy and recorded background.

Cardiac mapping systems, such as the St. Jude Medical Ensite™ Velocity™ Cardiac Mapping System (Ensite), represent established 3-D electroanatomical mapping systems that are used for point-by-point mapping of the electrical state of different cardiac chambers. During a mapping procedure, a roving catheter is moved around a chamber of the heart and electrical activity is measured at each location for a period of time. The procedure is used to characterize the electrical behavior of the cardiac tissue, such as to find areas of low voltage, scar, focal points of arrhythmias, etc.

A need remains for methods and systems that improve the mapping of electrical and mechanical cardiac data.

SUMMARY

In accordance with embodiments herein, methods and systems are provided for equalizing cycle lengths among different map points during mapping studies. Different embodiments may be applicable to different circumstances and physiological settings. A compression embodiment encapsulates the entire behavior of a map point throughout its native cycle length. A truncation and rotation embodiment and an extension and rotation embodiment allow for physiologically-relevant processing of the motion data.

In accordance with embodiments herein, a method is provided to analyze data of a region of interest in connection with cardiac mapping. The method comprises utilizing one or more processors for acquiring data recordings of motion data with a navigation system motion sensor in contact with the region of interest for determining cycle lengths associated with cardiac events in the data recordings and for equalizing cycle lengths among different map points for a region of interest.

DETAILED DESCRIPTION

Figure 1:
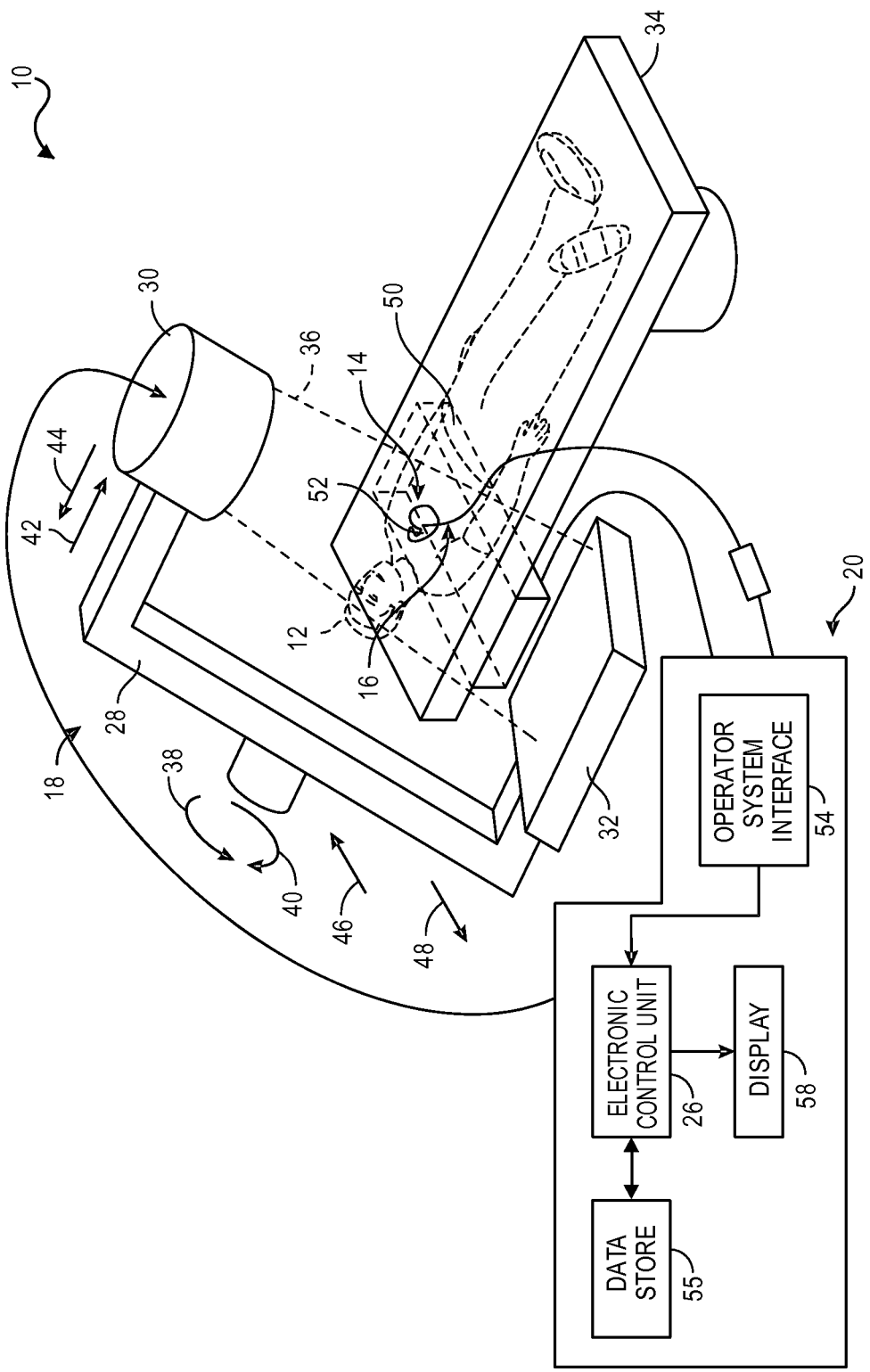
FIG. 1 illustrates an imaging and navigation system of an embodiment.

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Throughout the present disclosure, the terms beat, cardiac cycle, event and cardiac event are used interchangeably to refer to a single complete cardiac cycle of the heart, such as from the cycle beginning at the start of an intrinsic or paced atrial event (e.g., the P-wave) and continuing until the beginning of the next intrinsic or paced atrial event (e.g., next P-wave).

The term cycle length is used to refer to a time period between a characteristic of interest in consecutive cardiac cycles, such as consecutive R-waves, P-waves, T-waves, and the like.

Embodiments herein may be implemented with, and/or utilize aspects of, the methods and system described in the following applications:

- U.S. patent application Ser. No. 14/328,523, filed Jul. 10, 2014, titled "METHOD AND SYSTEM TO ASSESS MECHANICAL DYSSYNCHRONY BASED ON MOTION DATA COLLECTED BY A NAVIGATION SYSTEM", now U.S. Pat. No. 9,301,713,
- U.S. patent application Ser. No. 14/328,513, filed Jul. 10, 2014, titled "METHOD AND SYSTEM TO MEASURE CARDIAC MOTION USING A CARDIOVASCULAR NAVIGATION SYSTEM", now U.S. Pat. No. 9,314,191,
- U.S. patent application Ser. No. 14/478,707 U.S. Pub. No. 2015/0141765, filed Sep. 5, 2014, titled "METHOD AND SYSTEM TO IDENTIFY MOTION DATA ASSOCIATED WITH CONSISTENT ELECTRICAL AND MECHANICAL BEHAVIOR FOR A REGION OF INTEREST",
- U.S. patent application 61/988,779, filed May 5, 2014, titled "METHODS AND SYSTEMS TO CALCU- LATE TIME OF MECHANICAL ACTIVATION USING CHARACTERIZATION MOTION DATA AREA STRAINS", U.S. patent application Ser. No. 14/270,181, filed May 5, 2014, titled "METHOD AND SYSTEM TO CHARACTERIZE MOTION DATA BASED ON NEIGHBORING MAP POINTS", now U.S. Pat. No. 9,364,170, U.S. patent application Ser. No. 14/270,186 U.S. Pub. No. 2015/0313480, filed May 5, 2014, titled "METHOD AND SYSTEM FOR CALCULATING STRAIN FROM CHARACTERIZATION DATA OF A CARDIAC CHAMBER", U.S. patent application Ser. No. 14/270,176, filed May 5, 2014, titled "METHOD AND SYSTEM FOR DISPLAYING A THREE DIMENSIONAL VISUALIZATION OF CARDIAC MOTION", now U.S. Pat. No. 9,380,940, U.S. patent application 61/988,735, filed May 5, 2014, titled "METHOD AND SYSTEM TO DETERMINE CARDIAC CYCLE LENGTH IN CONNECTION WITH CARDIAC MAPPING", U.S. patent application 61/988,767, filed May 5, 2014, titled "METHOD AND SYSTEM TO SUBDIVIDE A MAPPING AREA FOR MECHANICAL ACTIVATION ANALYSIS", U.S. patent application 61/988,771, filed May 5, 2014, titled "CARDIAC RESYNCHRONIZATION SYSTEM AND METHOD", and U.S. patent application 61/988,774, filed May 5, 2014, titled "SYSTEM AND METHOD FOR EVALUATING LEAD STABILITY OF AN IMPLANTABLE MEDICAL DEVICE".

All of the above cited applications are expressly incorporated herein by reference in their entirety.

FIG. 1 illustrates a cardiovascular navigation system 10, for use in imaging an anatomical region of a patient 12 such as a heart 14 in accordance with embodiments herein. A medical tool 16 is placed within the anatomical region, such as for example, an electrophysiological (EP) mapping catheter or a catheter generally described or shown in U.S. Pat. No. 7,881,769, the entire disclosure of which is incorporated herein by reference. The medical tool 16 includes a plurality of electrophysiological sensors 52 that may be placed on the endocardial or epicardial surface of the left ventricle of the heart 14. The electrophysiological sensors 52 may be attached to the distal or proximal end of the medical tool 16, or any point in between. The electrophysiological sensors 52 measure a position and an electrical potential or electric current of biological cells and tissues, and are transmitted to an electronic control unit (ECU) 26. For example, the electrophysiological sensors 52 may be positioned by the medical tool 16 to measure the electrical potential along a portion of the wall of the heart 14. It should be understood, however, that the electrophysiological sensors 52 could be used in a variety of anatomical regions within the heart 14 or other organs in which motion characterization may be of interest. Additionally or alternatively, the electrophysiological sensors 52 may be replaced by separate motion sensors and electrical sensors. Optionally, ECU 26 may receive position and electrical sensor measurements simultaneously from motion sensors and electrical sensors.

System 10 may include an imaging system 18 and a mapping system 20. The system 10 may also include a registration system for registering a group of images of the anatomical region of patient 12 in a navigation coordinate system of the mapping system 20 as generally described and shown in U.S. Patent Publication 2013/0272592 and International Pub. No. WO 2012090148, each of which is entirely incorporated herein by reference.

The imaging system 18 may be provided to acquire images of heart 14 or another anatomical region of interest and comprises a fluoroscopic imaging system in the illustrated embodiment. Additionally or alternatively, rather than a fluoroscopic imaging system, a computed tomography (CT) imaging systems, three-dimensional radio angiography (3DRA) systems and the like may be used. Although the imaging system 18 is described herein for an embodiment of the invention, the imaging system 18 is not required for the inventive subject matter described within this application.

The imaging system 18 may include a C-arm support structure 28, a radiation emitter 30, and a radiation detector 32. Emitter 30 and detector 32 are disposed on opposite ends of support structure 28 and disposed on opposite sides of patient 12 as patient 12 lays on an operation table 34. Emitter 30 and detector 32 define a field of view 36 and are positioned such that the field of view 36 includes the anatomical region of interest as patient 12 lays on operation table 34. Imaging system 18 is configured to capture images of anatomical features and other objects within field of view 36. The C-arm support structure 28 may have freedom to rotate about the patient as shown by lines 38, 40. The C-arm support structure 28 may also have freedom to slide along lines 42, 44 (i.e. along the cranio-caudal axis of patient 12) and/or along lines 46, 48 (i.e. perpendicular to the cranio-caudal axis of patient 12). Rotational and translational movement of support structure 28 yields corresponding rotational and translational movement of field of view 36.

Imaging system 18 may acquire a group of images of an anatomical region of patient 12 by first shifting along lines 42, 44, 46, 48 to place the anatomical region of interest within the field of view 36. Second, the C-arm support structure 28 may rotate radiation emitter 30 and radiation detector 32 about patient 12, keeping the anatomical region within field of view 36. Imaging system 18 may capture images of the anatomical region as support structure 28 rotates, providing a group of two-dimensional images of the anatomical region from a variety of angles. The group of images may be communicated to ECU 26 for image processing and display. The group of images may comprise a sequence of images taken over a predetermined time period.

Mapping system 20 may be provided to determine the position and orientation of medical tool 16 within the body of patient 12 and to permit a clinician to navigate the medical tool 16 within the body. In the illustrated embodiment, system 20 comprises a magnetic navigation system in which magnetic fields are generated in the anatomical region and position sensors associated with tool 16 generate an output that changes responsive to the position of the sensors within the magnetic field. System 20 may comprise, for example, the systems generally shown and described in, for example, U.S. Pat. Nos. 6,233,476, 7,197,354, 7,386,339, and 7,505,809, all of which are incorporated by reference in their entirety. Although a magnetic navigation system is shown in the illustrated embodiment, it should be understood that the invention could find use with a variety of navigation systems including those based on the creation and detection of axes specific electric fields. Mapping system 20 may include a transmitter assembly 50.

The transmitter assembly 50 is conventional in the art and may include a plurality of coils arranged orthogonally to one another to produce a magnetic field in and/or around the anatomical region of interest. It should be noted that, although transmitter assembly 50 is shown under the body of patient 12 and under table 34 in FIG. 1, transmitter assembly 50 may be placed in another location, such as attached to radiation emitter 30, from which the magnetic field generators can project a magnetic field in the anatomical region of interest. In accordance with certain embodiments, the transmitter assembly 50 is within the field of view 36. The ECU 26 may control the generation of magnetic fields by transmitter assembly 50.

The electrophysiological sensors 52 are configured to generate an output dependent on the relative position of electrophysiological sensors 52 within the field generated by transmitter assembly 50. In FIG. 1, the electrophysiological sensor 52 and medical tool 16 are shown disposed around the heart 14. As medical tool 16 is guided to and through the region of interest, the mapping system 20 determines the location of the electrophysiological sensors 52 in the generated field, and thus the position of medical tool 16 as well. The mapping system 20 further determines a navigation coordinate such as a cartesian coordinate (e.g., (X, Y, Z)), of the navigation coordinate system.

One or more patient reference sensors (not shown) are on the body of the patient 12, for example, on the chest. The patient reference sensors (PRS) measure a displacement and orientation of the patient reference sensors relative to a predetermined reference point, such as, the electrophysiological sensors 52 or the transmitter assembly 50.

The ECU 26 of the mapping system 20 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 26 may receive a plurality of input signals including signals generated by medical tool 16, imaging system 18, the electrophysiological sensors 52, an operator system interface 54, and the patient reference sensors and generate a plurality of output signals including those used to control tool 16, imaging system 18, the display 58. The operator system interface 54 may include a keyboard, a keypad, buttons, a touchscreen, a monitor, a mouse, and the like. ECU 26 may also receive an input signal from an organ monitor (not shown), such as an ECG monitor, and sort or segregate images from imaging system 18 based on a timing signal of a monitored organ. For example, ECU 26 may sort images based on the phase of the patient's cardiac cycle at which each image was collected, as more fully described in U.S. Pat. No. 7,697,973, which is hereby incorporated by reference in its entirety.

The mapping system 20 includes a data store 55 to store, among other things, the original motion data, modified motion data and instructions to direct one or more processors to perform the operations described herein.

The methods described herein may be implemented as software or a system that directs one or more hardware circuits or circuitry to perform the actions described herein. For example, the operations of the methods may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into circuits.

Motion mapping refers to the use of the mapping system 20 in which a map-enabled catheter is moved around an anatomical structure and the 3-D position is recorded for a period of time (i.e. 30 seconds) at each location. Motion can then be characterized by analyzing movement of the various map points in relation to each other. The map-enabled catheter may be moved around the entire LV endocardium, in order that movement of the entire LV may be assessed. Alternatively or additionally, the map-enabled catheter may be inserted into veins that are candidates for LV lead placement. Movement of the portion of the LV spanned by these veins can then be assessed. However, it is to be understood that the present disclosure is not limited to use with electrical/motion data collected by the mapping system 20, but instead embodiments of the present disclosure may be used with any system that is able to collect electrical and/or motion data at map points across the surface of the heart (endocardial and/or epicardial).

The system 20 noted above utilizes measurements of the time of local electrical or mechanical activation by considering individual beats at each map point. For example, the system 20 may buffer ten or more cardiac beats and allow the user to choose one of the ten or more beats for mapping. However, when the user is choosing the beat, the user may not have a global view into the beats at the other map points. During a mapping procedure, there may be large variability in cycle lengths (CL) between consecutive beats in a recording at each map point as well as variability in CLs between different map points. This variability may be introduced by different sedation states of the patient or administration of various drugs during the procedure. With different levels of sedation and the administration of various drugs, the heart and respiratory rates may vary during motion mapping from one map point to the next. However, characterization of motion at different map points (both quantitatively and qualitatively) and depicting an overall description of motion abnormalities require resolution of cycle length differences among all map points.

In accordance with embodiments herein, methods and systems are disclosed for equalization of cycle lengths among different map points to enable simultaneous analyses or visualization of motion behavior throughout the cardiac chamber of interest. In accordance with embodiments herein, methods and systems are disclosed that utilize techniques that enable the selection of a strategy for cycle length equalization.

While the present disclosure discusses equalization in connection with raw x, y, z positional signals from the navigation system, it is understood that the same techniques can be applied to any other processed signals using the raw positional signals including displacement, strain, velocity, acceleration, etc. Further, it is understood that embodiments herein may be implemented in connection with any coordinate system, including a patient-specific cardiac coordinate system with radial, longitudinal and circumferential dimensions. It is also understood that the techniques described herein can be used with any motion mapping method or system in connection with any chamber of the heart.

Figure 2:
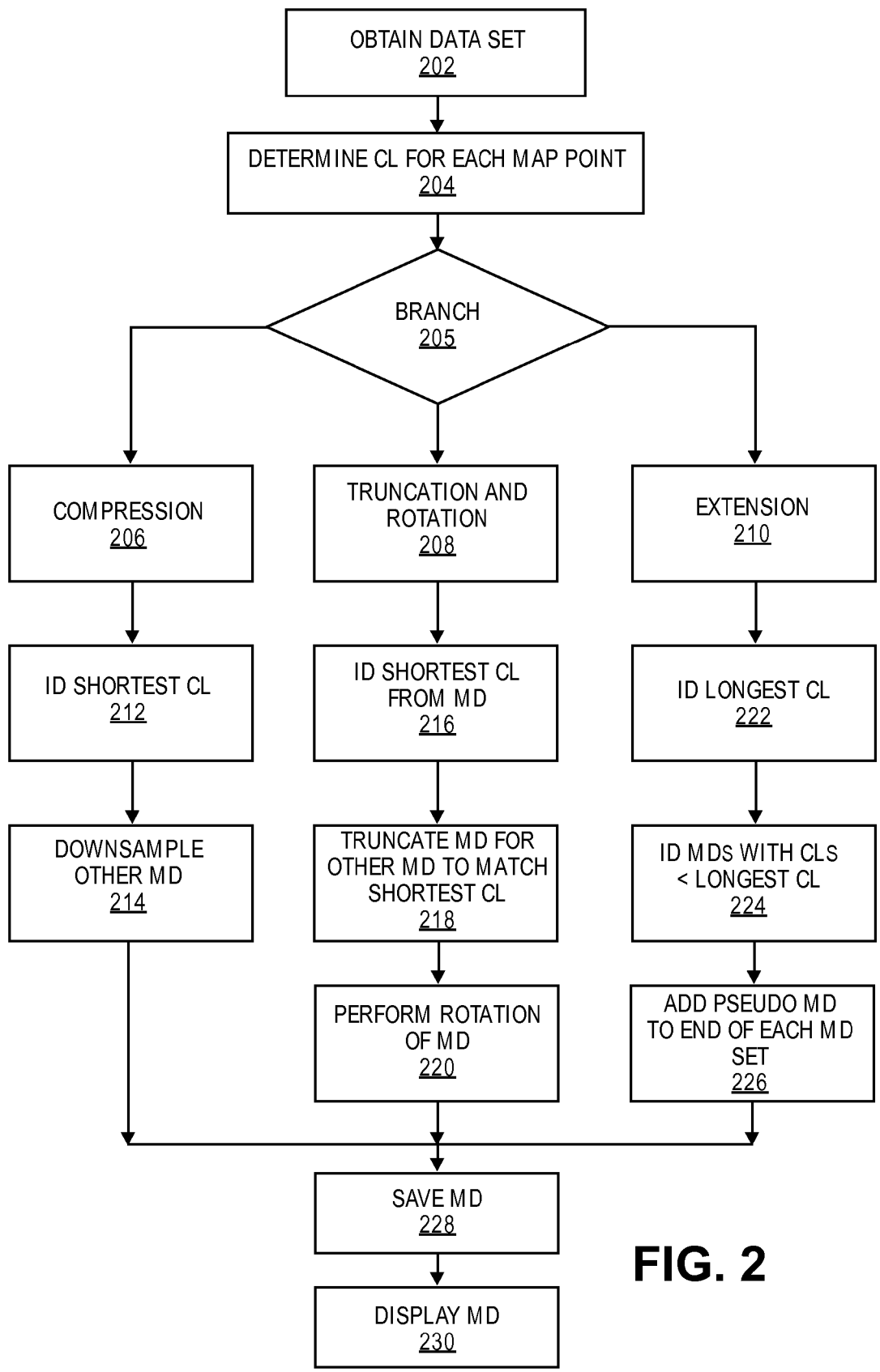
FIG. 2 illustrates a process for equalizing cycle length between multiple map points in accordance with embodiments herein.

FIG. 2 illustrates a process for equalizing cycle length between multiple map points in accordance with embodiments herein. At 202, the method obtains a data set for the map points for a region of interest in the heart. For example, the mapping system 20 may collect the data set for the map points. For example, mapping system 20 may collect a data set that includes motion data collected over one or more cardiac cycles at each of a select number of map points distributed across the left ventricle. Optionally, the mapping system 20 may collect a data set that includes electrical activity data collected over one or more cardiac cycles at each of a select number of map points distributed across the left ventricle. Optionally, the data set may include both motion and electrical activity data collected for the same, partially different or entirely different groups of map points. Optionally, the data set may include motion and/or electrical activity data for each map point collected for a single cardiac cycle at each map point.

During electrical and/or motion (mechanical) data collection, data recordings are made and stored in memory for several map points in the heart. Each data recording lasts for some select period of time (i.e. one cardiac cycle, 30 seconds) and includes electrical/motion data collected in connection with one or multiple heart beats, the number depending on the heart rate. The heart rate may vary within each recording and between recordings.

At 204, the method determines a plurality of cycle lengths (CL) in connection with a first map point. When a data recording for motion and/or electrical data are collected for more than one cardiac cycle at any one map point, the method determines a single cycle length to be associated with each map point. The plurality of CL's are then combined to form a single CL for the associated map point. For example, the single CL may be an ensemble average of the CLs from the data recording for the map point. Optionally, the single CL may be chosen from the CLs for the data recording, such as the most frequent CL, the mean CL, or otherwise.

The motion data is pre-processed to compensate for patient movement, changes in the C-arm angulation, and respiration. The motion data may undergo electrical beat parsing to provide consistent rhythm of the selected beats and the motion data for selected beats may be ensemble-averaged to obtain a single representative set of motion data (e.g., x, y, z locations) per map point. Alternatively, a single cardiac cycle per map point may be selected. The motion signals from single beats and/or ensemble-averaged signals are synced to a select characteristic of interest such as to a start with the peak of the R-wave or another cardiac feature on a particular surface ECG lead.

As described herein, different techniques may be utilized for equalization of cardiac cycles among different map points that enable a simultaneous comparison of all, or a select group of, map points in the presence of variable heart rates. For example, the equalizing operation includes identifying a select cycle length from the cycle lengths and modifying the motion data to have a common number of motion data samples for each map point. For example, the equalizing operation generates an equalized motion data set having a common number of motion data samples for each map point. For example, a compression process may be used when it is assumed that effects of varying cycle length are generally the same on both systolic and diastolic phases of the cardiac cycle. As another example, a truncation and rotation process may be used when it is assumed that the effects of varying cycle length primarily or only effect the diastolic phase of the cardiac cycle. As another example, an extension and rotation process may be used when it is assumed that the effects of varying cycle length primarily or only effect the diastolic phase of the cardiac cycle.

Figure 3:
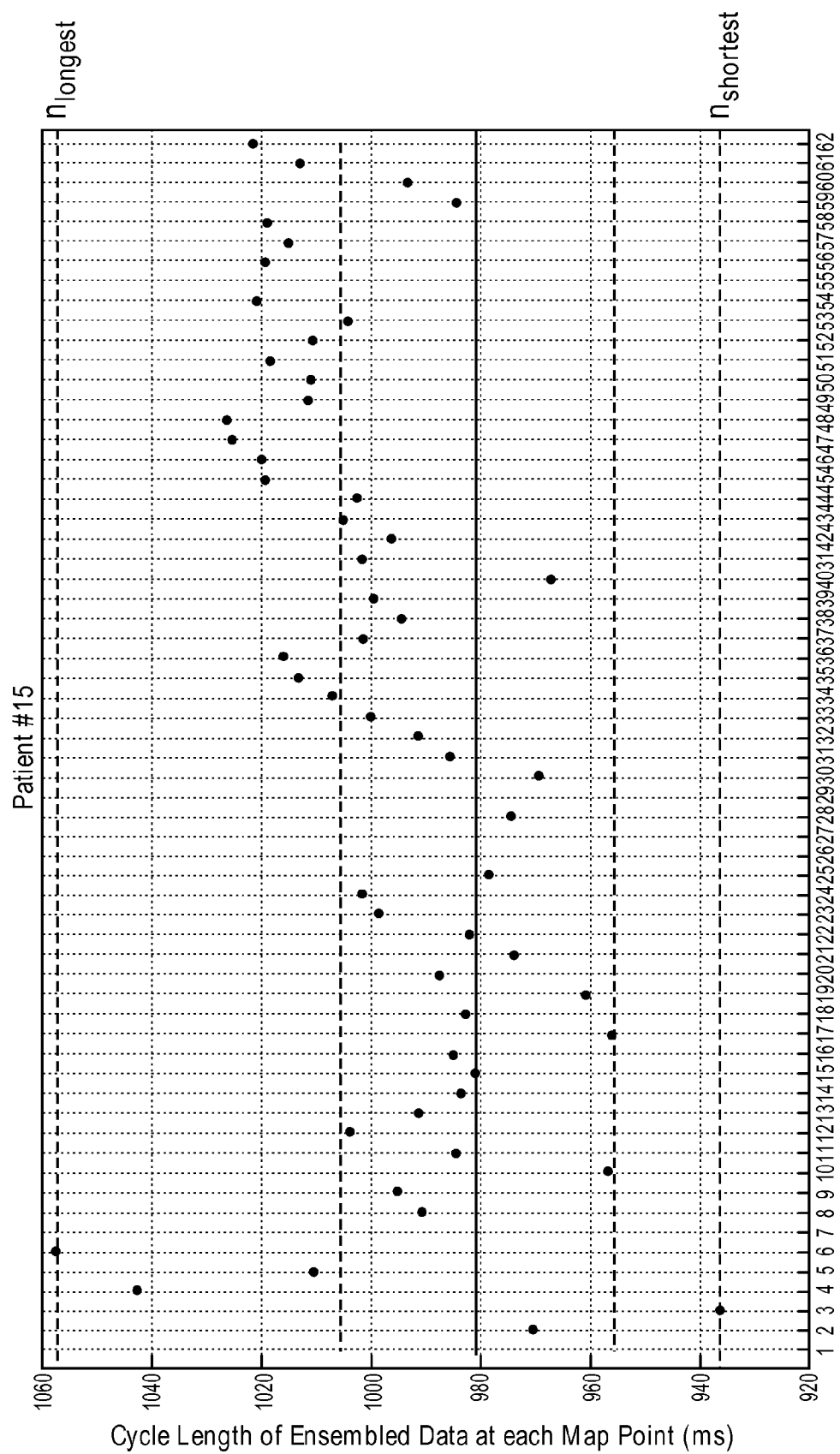
FIG. 3 illustrates cycle length variability among map points (events) associated with the motion data set collected for a given patient.

FIG. 3 illustrates an example of cycle length variability among map points (events) associated with a motion data set collected for a given patient. In the example of FIG. 3, there is a range of cycle lengths of 935-1060 ms among the map points between $n_{shortest}$ and $n_{longest}$. At different points during a data collection procedure, the patient is under the influence of different drugs and is at different sedation states. This results in some variability in the heart rate (and therefore, cycle length) at different recordings and different map points as shown in FIG. 3.

In order to facilitate analysis and visualization of the different map points that may exhibit different cycle lengths, processes are disclosed for different techniques that result in a common cycle length for all or a group of map points. In FIG. 2, different branches 206, 208, 210 may be used based on different effects of heart rate variability on the systolic and diastolic phases of the cardiac cycle.

At 205, in order to determine which branch 206, 208 and 210 to follow, the process may implement one or more of the following tests before an equalization strategy is selected. A correlation test may be performed based on mathematical convolution between the shortest cycle length and the motion data from each of the other map points to indicate the level of similarity in signal (waveform) morphology. An equalization technique based on truncation or extension may be used if there is at least a pre-defined Correlation Threshold (CT) such as 85% between the map point of interest and the shortest signal. If the correlation is less than the CT, then the compression technique at 206 may be used.

For each map point, defining a flatness score (FS) as the difference between the max and the min value of the motion data (in any dimension) during the diastolic phase, determines the degree of stability during diastole. Equalization techniques based on truncation or extension may not be used if the FS is larger than a pre-defined limit such as 2 mm. In that case, compression techniques may be used.

Considerations of the time of mechanical activation (which can be based on the time for a point to reach its most inward location or a percentage of that displacement) indicate the effect of heart rate on systolic duration. In the case of a difference larger than a pre-defined threshold such as 150 ms in the timing of mechanical activation between the map points with the shortest and the longest cycle lengths, an equalization technique based on compression may be used.

If the difference in cycle length is too large between $n_{longest}$ and $n_{shortest}$ such that for example $$\frac{n_{longest}}{n_{shortest}} \geq 3$$

a combination of truncation and compression may be used. In this case, the longer map points are first truncated to their respective points of end-systole. The end-systolic sample is defined as the sample after which point the variation in signal amplitude is less than a pre-defined threshold such as 2 mm, similar to FS defined above. After truncation of all longer cycle lengths to their respective end-systolic points, all map points are compressed to match $n_{shortest}$.

At 206, the process applies an equalizing or a compression operation. The compression/equalizing operation includes identifying a select cycle length from the plurality of cycle lengths and down-sampling the motion data for the map points throughout the cycle lengths to produce a down sampled motion data set having a same number of motion data samples for each of the map points. The operation at 206 is utilized when the changes in the heart rate are expected to be small enough such that the effects on the systolic and diastolic phases of the cardiac cycle are similar. In particular, the compression technique involves a homogenous down-sampling of the motion data in map points with longer cycle lengths. At 212, the shortest cycle length ($n_{shortest}$) of motion data among all map points of interest is found. The shortest CL represents one type of select CL that may be identified. The select CL may be an average CL, mean CL and the like.

At 214, the motion data from all other map points with more sample points than $n_{shortest}$ are down-sampled equally throughout the length of the cardiac cycle. The down sampling is accomplished by defining a frame rate (FR) which can be any integer, less than or equal to $n_{shortest}$. Then, the length of the sample points of interest (x) is divided by FR and the samples at indices rounded to the nearest integer less than or equal x/FR are selected to represent the compressed motion data samples signal. This approach produces a down-sampled motion data set having the same number of motion data samples as $n_{shortest}$ for each of the map points, while still capturing the mechanical behavior throughout the entire cardiac cycle.

Alternatively, at 208, flow may branch to perform a truncation and rotation process. The truncation and rotation is applied when it is expected that beats with longer cycle lengths have the same systolic behavior as beats with shorter cycle lengths. In other words, the flow at 208 assumes that changes in the heart rate affect only the diastolic phase of the cardiac cycle such that a faster heart rate results in a shortening of only the diastolic phase without any effects on the systolic phase of the cardiac cycle.

At 216, a select cycle length is identified. For example, a shortest cycle length ($n_{shortest}$) of the motion data among all map points of interest may be found.

At 218, the motion data from map points with cycle lengths greater than $n_{shortest}$ are truncated to have the same number of sample points as in the motion data for the map point with the shortest CL $n_{shortest}$. In other words, only the first $n_{shortest}$ samples are considered. For example, the equalizing operation truncates motion data samples associated with an ending position of the diastolic phase that occurs after the select cycle length.

At 220, a rotational step can also be implemented to ensure a periodic behavior of the truncated motion data samples. The motion data defines a displacement waveform in connection with each of the map points. The equalization operation includes rotating motion data samples from the motion data to shift the displacement waveforms after a reference point to an end of the cardiac cycle. The rotation technique may be implemented in accordance with the above referenced provisional and utility applications incorporated by reference herein. For example, at 220, the method applies a rotation technique to the displacement waveform. The displacement waveform may exhibit non-periodic behavior such that the value of the displacement at the normalization time is not equal to the displacement value at the end of the cardiac cycle. The non-periodic behavior may be due to, for example, measurement error of the motion (e.g., the electrophysiological sensors) or the patient reference sensor, shifts in the position of the medical tool during cardiac cycles, gradual changes in respiratory frequencies, or the like. To correct for this non-periodicity, the ECU 26 (FIG. 1) applies the rotation technique to the displacement waveform. The rotation technique shifts the displacement waveform after a set reference point to the end of the cardiac cycle using, for example, a linear scale such that the shifting of the displacement waveform increases approaching the end of the displacement waveform at the cardiac cycle. The reference point may be the first anchor, the normalization time or the peak reference, or the second anchor, the end of the cardiac cycle, or the like.

Before rotation, the ECU 26 determines two anchor points of the displacement waveform. A first anchor is at the displacement waveform at a corresponding normalization time. A second anchor is at the displacement waveform at the end of the cardiac cycle. The ECU 26 rotates or shifts the displacement waveform at the first anchor or reference point, linearly increasing the shifting magnitude until the second anchor has a displacement value equal to the first anchor resulting in the rotated displacement waveform.

The mapping navigation system 20, determines a Cartesian coordinate system (e.g., (X, Y, Z)) representing the position measurements from the motion sensor (e.g., the electrophysiological sensor), the imaging system, and the patient reference sensors having a predetermined reference as the origin, such as the operation table or the patient reference sensors. Optionally, the position measurements may be converted using a matrix translation and rotation operations to a cardiac coordinate system which is described with respect to radial, longitudinal, and circumferential directions of the left ventricular (LV).

For example, the ECU 26 may determine a LV long axis in which an operator (e.g., Doctor) indicates the apex of the LV and the base of the mitral valve in each patient intraoperatively using fluoroscopy images or the electroanatomical map from the image system 18 via the operator system interface 54. Once the operator indicates the apex, the ECU records a time stamp. The operator then defines the mitral annulus using at least 4 equally spaced markers around the circumference of the mitral annulus. The ECU determines the position at each of the marked timestamps to obtain the three dimensional position of the patient-specific anatomical markers. The long axis of the LV is then defined as the line connecting the apical point to the centroid of the mitral annulus points. Once the long axis of the LV is determined, the ECU converts the Cartesian coordinates of the position measurements of the motion sensor, the patient reference sensors, and/or the imaging system 18 to a cylindrical cardiac coordinate system by first determining a parallel vector (W) using the equation $\vec{W}=(\vec{Z}\cdot\vec{V})\vec{Z}$ (Equation 2)

In Equation 2, the variable Z is the longitudinal unit vector from the apex to the mitral annulus centroid, and V is a new unit vector that is in the direction of the minimum non-zero component of Z. Once the parallel vector is determined, the ECU 26 will determine a new unit vector, X, that is perpendicular to the longitudinal vector as shown in equation 3, and determine a new unit vector, Y, that is a cross-product of X and Z as shown in equation 4.

$$\vec{X}=(\vec{V}-\vec{W}) \qquad \text{(Equation 3)}$$

$$\vec{Y}=\vec{X}\times\vec{Z} \qquad \text{(Equation 4)}$$

Once the unit vectors are determined, the ECU 26 may determine the cylindrical cardiac coordinates (radial, circumferential, longitudinal) from the Cartesian coordinates using Equation 5.

$$\rho = \sqrt{x^2 + y^2} \qquad \text{(Equation 5)}$$
$$\theta = \tan^{-1}\left(\frac{y}{x}\right)$$
$$Z = Z$$

Figure 4:
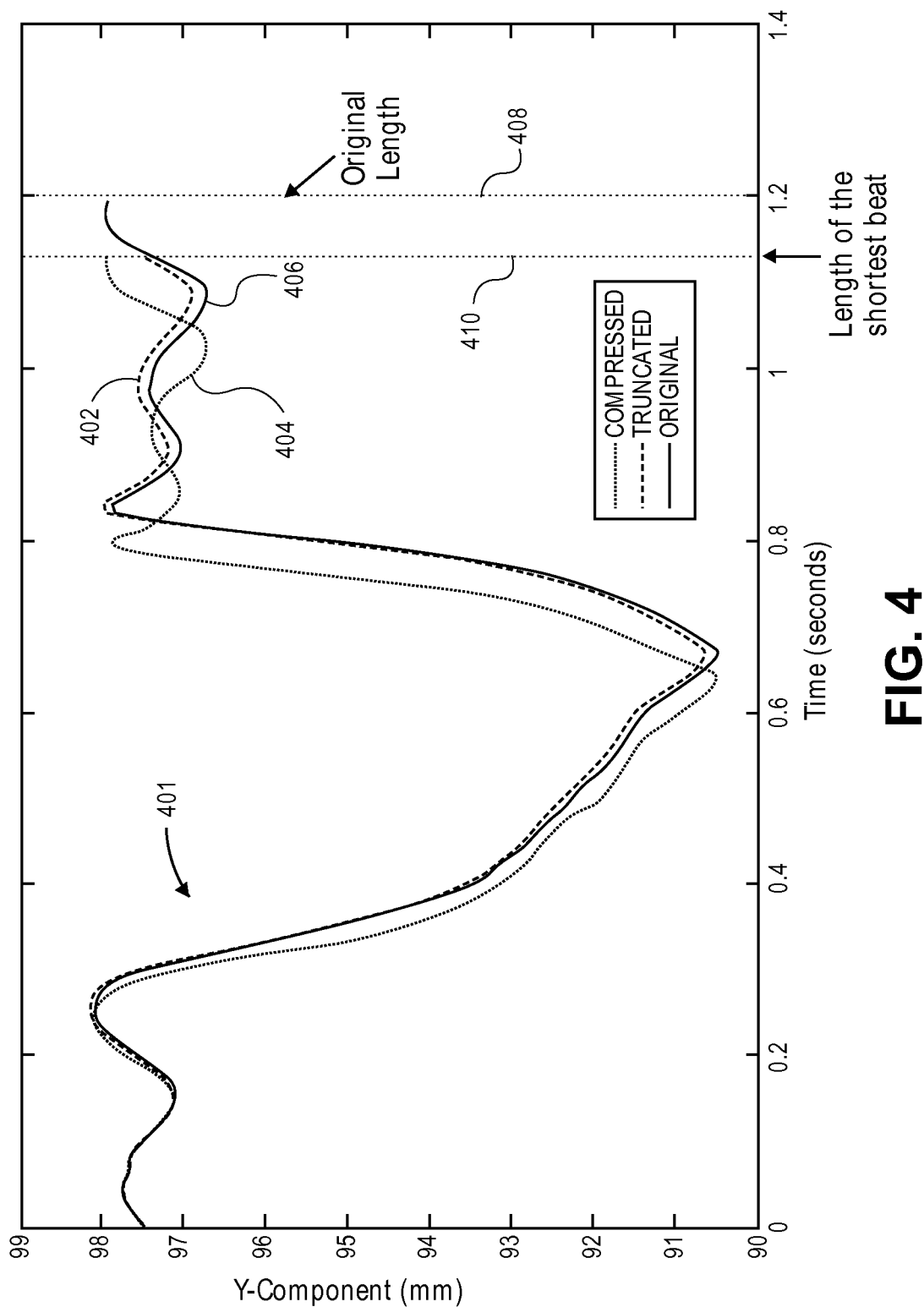
FIG. 4 illustrates a motion waveform defined by motion data collected over one cardiac cycle for an associated map point.

FIG. 4 illustrates a motion waveform 401 defined by motion data collected over one cardiac cycle/event/beat for an associated map point, which may be displayed to a user in accordance with certain embodiments. The vertical axis corresponds to displacement (in the Y direction) from a reference point, while the horizontal axis corresponds to time. FIG. 4 illustrates different approaches for shortening the longest beat by truncation 402 (dashed) and compression 404 (dotted) from the original motion waveform 406 having an original length 408 to the length of the shortest beat 410 throughout the entire recording. The compression 404 may be achieved using the operations at 206, 212, and 214 in FIG. 2. The truncation 402 may be achieved using the operations at 208, 216, 218, and 220.

Returning to FIG. 2, in accordance with flow path 210, the method performs an extension of the CL. Extension of the CL is conducted, when it is expected that beats with longer cycle lengths have the same systolic behavior as beats with shorter CLs and that changes in the heart rate primarily (or only) affect the diastolic phase of the cardiac cycle.

At 222, the longest CL of motion data for a map point is determined. At 224, map points with CLs shorter than the longest CL are identified. At 226, the cycle lengths shorter than the longest cycle length ($n_{longest}$) of motion data among all map points of interest are padded at the end with pseudo-motion data. For example, the pseudo-motion data may represent a repeat of the final diastolic value for the actual motion data to match $n_{longest}$. The pseudo-motion data may be calculated by extrapolation of actual motion data for the map point from other cardiac events, actual motion data from earlier in the same cardiac event, extrapolation of actual motion data from other map points, and the like.

At 228, the modified motion data for each map point is saved to form an extended motion data set, in which the motion data for each map point that has a common cycle length. With the above embodiments, all map points can exhibit the same length of time for the completion of a cardiac cycle, enabling any analysis or visualization technique that relies on a comparison among different map points.

Figure 5:
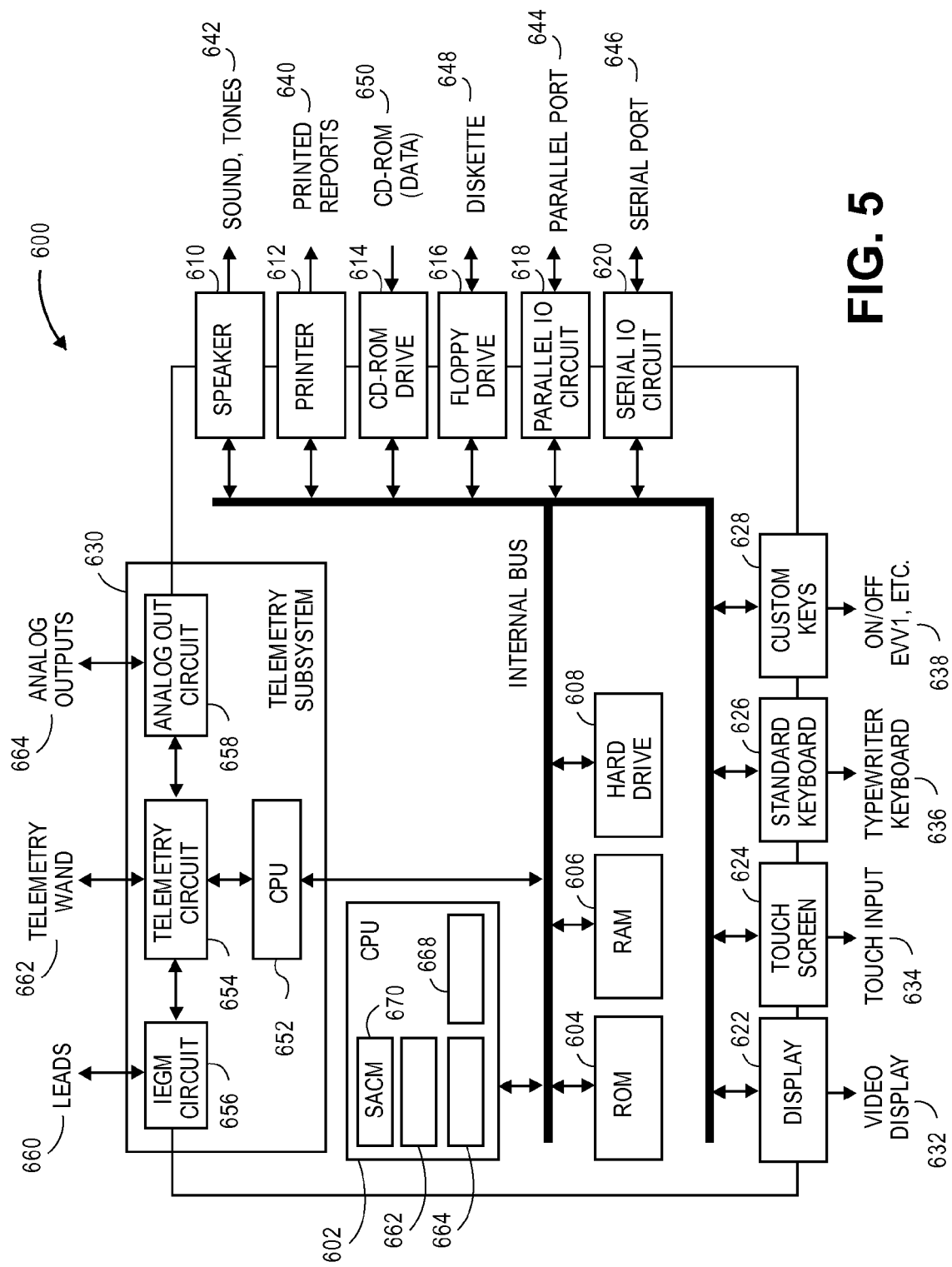
FIG. 5 illustrates a functional block diagram of an external device operated in accordance with the processes described herein.

At 230, the mapping system 20 displays the modified motion data on display 58 to the user. Optionally, the modified motion data may be displayed on display 622 of the external device 600 (FIG. 5). As an example, the modified motion data may be presented as shown in FIG. 4.

FIG. 5 illustrates a functional block diagram of an external device 600 that is operated in accordance with the processes described herein to analyze motion and electrical data and to interface with implantable medical devices (IMD). The external device 600 may implement the operations of the mapping system 20 and processes discussed herein in connection with FIG. 2. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 600 and with the IMD. The CPU 602 performs the processes discussed above. The CPU 602 may include RAM or ROM memory, logic and timing circuitry, state machine circuitry, and I/O circuitry to interface with the IMD. The display 622 (e.g., may be connected to the video display 632). The touch screen 624 may display graphic information relating to the IMD. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The CPU 602 is configured to analyze motion data and electrical measurement data collected by the cardiovascular navigation system and perform the prospective and retrospective analysis of cycle lengths as discussed herein.

The CPU 602 receives electrical/motion data (MD) sets, as explained herein and performs various analysis prior to, or after, the cycle length analysis discussed above in connection with FIGS. 2-5. The CPU 602 includes a subset analysis circuit module 662 that divides subsets of motion data into quadrants associated with corresponding phases of the cardiac cycle with raw electrical and motion data. The CPU 602 includes an electrical waveform analysis circuit module 664 that analyzes the electrical sensor measurements of the heart. The electrical waveform analysis circuit module 664 analyzes the electrical sensor measurements to locate ectopic beats within the electrical sensor measurement data. Once an ectopic beat is located, the analysis circuit module 664 removes the ectopic beat data from the motion data.

A position analysis circuit module 668 analyzes the position measurement of the heart based on at least two channels of the motion sensor. The position analysis circuit module 668 determines and locates inconsistent electrical/motion data based on the position measurements and removes the inconsistent data from the electrical/motion data.

The CPU 602 also includes a synchronization and averaging circuit module (SACM) 670. The SACM 670 receives the motion data from modules 664 and 668 and synchronizes the motion date for a corresponding map point. Once the motion data is synchronized, the SACM 670 calculates an average motion characterization waveform. The display 622 displays the average motion characterization waveform based on the calculations of the SACM 670.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to implantable leads to receive and process IEGM cardiac signals as discussed above. Optionally, the IEGM cardiac signals sensed by the leads may be collected by the IMD and then transmitted, to the external device 600, wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the IMD and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the IMD.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. A method to analyze data of a region of interest in order to generate a cardiac map, the method comprising:
   utilizing one or more processors:
   acquiring data recordings of motion data at each of a select number of map points for the region of interest with a navigation system motion sensor in contact with the region of interest;
   determining cycle lengths associated with cardiac events in the data recordings, wherein the determining operation includes determining a plurality of cycle lengths in connection with a first map point of the select number of map points;
   equalizing cycle lengths among different map points for the region of interest;
   modifying the motion data based on the equalizing operation; and
   displaying the modified motion data on a display.

2. The method of claim 1, wherein the equalizing comprises performing at least one of i) a compression process to encapsulate an entire behavior of at least one map point of the select number of map points throughout a native cycle length; ii) a truncation and rotation process; or iii) an extension and rotation process.

3. The method of claim 1, wherein the equalizing operation includes identifying a select cycle length from the plurality of cycle lengths and down-sampling the motion data for the map points throughout the cycle lengths to produce a down sampled motion data set having a same number of motion data samples for each of the map points.

4. The method of claim 1, wherein the equalizing operation includes identifying a select cycle length from the cycle lengths and modifying the motion data to have a common number of motion data samples for each map point.

5. The method of claim 4, wherein the equalizing operation truncates motion data samples from the motion data associated with an ending position of the diastolic phase that occurs after the select cycle length.

6. The method of claim 4, wherein the motion data defines displacement waveforms in connection with each of the map points, the equalization operation including rotating motion data samples from the motion data to shift the displacement waveforms after a reference point to an end of the cardiac cycle.

7. The method of claim 1, wherein the equalizing operation includes identifying a longest cycle length from the cycle lengths and padding the cycle lengths that are shorter than the longest cycle length by adding pseudo-motion data to the motion data associated with the shorter cycle lengths.

8. The method of claim 1, further comprising:
determining a shortest cycle length associated with cardiac events in the data recordings;
determining a correlation based on mathematical convolution between the shortest cycle length and the motion data from each of the other map points in order to determine a level of similarity in signal morphology of the map points; and
determining a difference between the correlation and a correlation threshold, wherein the equalizing operation is based on the difference between the correlation and the correlation threshold.

9. The method of claim 8,
wherein the equalizing operation comprises performing a compression process to encapsulate an entire behavior of at least one map point of the select number of map points throughout a native cycle length, if the correlation is equal to or more than the correlation threshold, and
wherein the equalizing operation comprises performing at least one of i) a truncation and rotation process; or iii) an extension and rotation process, if the correlation is less than the correlation threshold.

10. The method of claim 1, further comprising:
determining a shortest cycle length associated with cardiac events during diastole in the data recordings;
determining a longest cycle length associated with cardiac events during diastole in the data recordings;
determining a flatness score (FS) based on the difference between the longest cycle length and the shortest cycle length;
determining whether the FS is larger than a first pre-defined limit, wherein:
if the FS is larger than a first pre-defined limit, the equalizing operation comprises at least performing a compression process, and
if the FS is not larger that the first pre-defined limit, the equalizing operation comprises at least one of i) a truncation and rotation process; or iii) an extension and rotation process.

11. The method of claim 10, further comprising determining whether the FS is larger than a second pre-defined limit, wherein if the FS is larger than the second pre-defined limit, the equalizing operation comprises performing a combination of truncation and compression.

12. A method to analyze data of a region of interest in order to generate a cardiac map, the method comprising:
utilizing one or more processors:
acquiring data recordings of motion data at each of a select number of map points for the region of interest with a navigation system motion sensor in contact with the region of interest;
determining cycle lengths associated with cardiac events in the data recordings,
equalizing cycle lengths among different map points for the region of interest wherein the equalizing operation generates an equalized motion data set having a common number of motion data samples for each map point;
modifying the motion data based on the equalizing operation; and
displaying the modified motion data on a display.

13. A cardiac mapping system comprising:
a data storage configured to store data recordings of motion data at each of a select number of map points for a region of interest from a motion sensor in contact with the region of interest;
a processor configured to:
determine cycle lengths associated with cardiac events in the data recordings, wherein the processor is configured to determine a plurality of cycle lengths in connection with a first map point of the select number of map points;
equalize cycle lengths among different map points for the region of interest; and
modify the motion data based on the equalizing operation; and
a display configured to communicate the modified motion data to a user.

14. The system of claim 13, wherein the processor is configured to perform at least one of i) a compression process to encapsulate an entire behavior of at least one map point of the select number of map points throughout a native cycle length; ii) a truncation and rotation process; or iii) an extension and rotation process.

15. The system of claim 13, wherein the processor is configured to identify a select cycle length from the plurality of cycle lengths and down-sample the motion data for the map points throughout the cycle lengths to produce a down sampled motion data set having a same number of motion data samples for each of the map points.

16. The system of claim 13, wherein the processor is configured to generate an equalized motion data set having a common number of motion data samples for each map point.

17. The system of claim 13, wherein the processor is configured to identify a longest cycle length from the cycle lengths and pad the cycle lengths that are shorter than the longest cycle length by adding pseudo-motion data to the motion data associated with the shorter cycle lengths.

18. A cardiac mapping system comprising:
a data storage configured to store data recordings of motion data at each of a select number of map points for a region of interest from a motion sensor in contact with the region of interest;
a processor configured to:
determine cycle lengths associated with cardiac events in the data recordings;
equalize cycle lengths among different map points for the region of interest, wherein the processor is configured to identify a select cycle length from the cycle lengths and modify the motion data to have a common number of motion data samples for each map point; and modify the motion data based on the equalizing operation; and a display configured to communicate the modified motion data to a user.

19. The system of claim 18, wherein the processor truncates motion data samples from the motion data associated with an ending position of the diastolic phase that occurs after the select cycle length.

20. The system of claim 18, wherein the motion data defines displacement waveforms in connection with each of the map points, the processor rotating motion data samples from the motion data to shift the displacement waveforms after a reference point to an end of the cardiac cycle.

* * * * *